(12) United States Patent
Stefan

(10) Patent No.: US 12,396,744 B2
(45) Date of Patent: Aug. 26, 2025

(54) SURGICAL INSTRUMENT, STEERING GEAR THEREOF, AND METHOD OF REGULATING THE POSITION OF A STEERING RING OF THE STEERING GEAR

(71) Applicant: KARL STORZ SE & Co. KG, Tuttlingen (DE)

(72) Inventor: Jochen Stefan, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 566 days.

(21) Appl. No.: 17/869,900

(22) Filed: Jul. 21, 2022

(65) Prior Publication Data
US 2023/0034856 A1 Feb. 2, 2023

(30) Foreign Application Priority Data
Jul. 28, 2021 (DE) ...................... 10 2021 119 530.6

(51) Int. Cl.
*A61B 34/20* (2016.01)
*A61B 17/29* (2006.01)
(Continued)

(52) U.S. Cl.
CPC .............. *A61B 17/29* (2013.01); *A61B 34/35* (2016.02); *A61B 34/70* (2016.02);
(Continued)

(58) Field of Classification Search
CPC ......... A61B 17/29; A61B 34/35; A61B 34/70; A61B 2017/00314; A61B 2017/291;
(Continued)

(56) References Cited

U.S. PATENT DOCUMENTS 5,454,827 A 10/1995 Aust et al.
7,699,855 B2 4/2010 Anderson et al.
(Continued)

FOREIGN PATENT DOCUMENTS

DE 102019121092 A1 2/2021
WO WO 2014/004242 A1 1/2014

OTHER PUBLICATIONS

Office Action for corresponding German Patent Application No. 10 2021 119 530.6, mailed May 3, 2022.

*Primary Examiner* — Benjamin J Klein
*Assistant Examiner* — Alisha J Sircar
(74) *Attorney, Agent, or Firm* — Jason H. Vick; Amped IP LLC

(57) ABSTRACT

An exemplary embodiment provides a steering gear (13) for a surgical instrument (1), which can be arranged at the proximal end (3) of a shaft (2) that defines a longitudinal axis (B) and has a bending mechanism (9) at the distal end (5). The steering gear (13) has two controllable and adjustable motorised drives and is designed to transfer the adjustment angles of the two controllable and adjustable motorised drives to a spatial alignment of a swash plate (14) which is designed to control the distal bending mechanism (9) of the surgical instrument (1). The swash plate (14) is arranged in a steering ring (19), and each of the two controllable and adjustable motorised drives has a drive shaft (17a, 17b) driven by a motor (17, 17'), each of which is connected to the steering ring (19) directly and operatively connected via a force transmitter (16, 16'), wherein the two force transmitters (16, 16') which are arranged on the drive shafts (17a, 17b) each define a drive axis (C, C'), directly contacting the steering ring (19) at an effective section (W). The steering ring (19) is cardanically suspended on a fastening device which has position sensors (23, 24, 25) on its cardan axes. Furthermore, a surgical instrument (1) with a steering gear (Continued)

(13) and a method for controlling the position of a steering ring (19) of a steering gear (13) are disclosed.

9 Claims, 5 Drawing Sheets

(51) Int. Cl.
*A61B 34/00* (2016.01)
*A61B 34/35* (2016.01)
*A61B 17/00* (2006.01)
*A61B 34/30* (2016.01)

(52) U.S. Cl.
CPC ............... *A61B 2017/00314* (2013.01); *A61B 2017/291* (2013.01); *A61B 2034/306* (2016.02)

(58) Field of Classification Search
CPC ........ A61B 2034/306; A61B 2090/067; A61B 34/30; A61B 2017/00017; A61B 2017/00327; A61B 2017/00398; A61B 2034/302; A61B 34/71
See application file for complete search history.

(56) References Cited

U.S. PATENT DOCUMENTS

| | | |
|---|---|---|
| 10,105,128 B2 | 10/2018 | Cooper et al. |
| 2015/0321343 A1 | 11/2015 | Armand et al. |
| 2021/0038331 A1 | 2/2021 | Grüner |
| 2022/0071724 A1* | 3/2022 | Heiliger ................ A61B 34/74 |

* cited by examiner

SURGICAL INSTRUMENT, STEERING GEAR THEREOF, AND METHOD OF REGULATING THE POSITION OF A STEERING RING OF THE STEERING GEAR

CROSS-REFERENCE TO RELATED APPLICATIONS

This application claims the benefit under 35 U.S.C. 119(a) to German Patent Application No. 10 2021 119 530.6, filed 28 Jul. 2021, the disclosure of which is incorporated herein by reference in its entirety.

BACKGROUND

An exemplary embodiment relates to a steering gear of a surgical instrument for bending a tool tip by means of a spatially adjustable swash plate, a surgical instrument that has such a steering gear, and a method for controlling the position of a steering ring of the steering gear.

Surgical instruments are known from the prior art which can be guided manually or by a robot and which have tools whose tool tip can be pivoted by means of various pivoting members engaging in one another. These pivot links are connected to a variety of steering wires or cords to provide fine control of the tool tip. A more even force distribution in all bending directions can be achieved with many thin steering wires compared to a few thicker steering wires.

Coupling such steering wires to a spatially adjustable disk which is arranged in an actuation unit on the proximal side and which is connected via a rod to a manually actuable control lever is known from U.S. Pat. No. 5,454,827, so that a movement of the spatially adjustable swash plate results in a corresponding relative movement of the distal-side pivoting elements and thus causes the tool tip to pivot.

The design of the drive for the steering wires with the spatially adjustable swash plate, on which all four steering wires are mounted, has the advantage that this enables a spatially compact design and only one component has to be moved in order to be able to address all steering wires. This construction means that only a small number of steering wires can be used, and that the spatially adjustable disk that drives the steering wires has to be operated manually, both of which affect the sensitivity and repeatability of the movement of the distal pivoting members.

It is also known that in a surgical instrument with a compact steering gear, the setting angles of two drives can be transmitted directly to the swash plate in order to align them for controlling the tool tip. For this purpose, steering wires are attached to the swash plate so that the tool tip can be steered continuously and smoothly by aligning the swash plate. For this purpose, the known steering gear has two drive bevel gears offset from one another by 180°, which are arranged on a common axis of rotation, which runs perpendicular to a longitudinal axis of the instrument, and each are coupled to an associated motor. The swash plate is arranged between the drive bevel gears and mounted in a steering ring which is non-rotatably connected to a third bevel gear which meshes with both drive bevel gears and is rotatable about an axis of rotation which is perpendicular to the longitudinal axis of the instrument and perpendicular to the common axis of rotation of the drive bevel gears. The interlocking chain is supplemented by a fourth bevel gear, which is arranged on the axis of rotation of the third bevel gear offset by 180° to the third bevel gear and meshes with both drive bevel gears, wherein the steering ring is freely and rotatably mounted in the fourth bevel gear. In this way, a closed gearing is formed, which ensures the engagement of all bevel gears with each other and enables an even distribution of power.

The design of the drive for the steering wires with the spatially adjustable swash plate, on which all steering wires are mounted, has the advantage that this enables a spatially compact design and only one component has to be moved in order to be able to address all steering wires.

U.S. Pat. No. 7,699,855 B2 discloses a surgical instrument which has an interface in order to be able to connect the instrument to a robotic arm. All drives that control the instrument are arranged in the robotic arm. The angle of rotation of the drives to the instrument is transmitted via coupling disks in a common separating plane. WO 2014/004242 A1 also describes such an interface, with the drives being installed in the robot arm. The above constructions are associated with a complex structure and indirect control. The drives are not arranged directly in the surgical instrument, which means that the swash plate is not controlled in a linear manner.

U.S. Pat. No. 10,105,128 B2 also discloses a control of such a tool tip; there this is done via a mechanism that includes toothed disk segments and link rods in order to transmit the movement of the drives to the swash plate.

Due to the structurally complex structure, control and regulation of the drives are also complex.

Given this state of the art, an exemplary embodiment is to provide a controllable and adjustable steering gear that enables precise guidance of the steering ring and is less complex.

This problem is solved by a steering gear with the features of claim 1.

The additional task of providing a surgical instrument that allows the guide ring to be guided precisely is achieved by the surgical instrument having the features of independent claim 7.

The further object of precisely controlling the guidance of the steering ring of a steering gear is solved by the method with the features of independent claim 9.

Developments of the steering gear, the surgical instrument and the method are set out in the respective dependent claims.

According to a first embodiment of the steering gear, it is designed to operate a surgical instrument. This can be arranged at the proximal end of a shaft which defines a longitudinal axis B and has a bending mechanism at the distal end. The steering gear has two motorised drives that can be controlled and adjusted, and is designed to transfer the adjustment angles of the two drives to a spatial alignment of a swash plate. The swash plate is also configured to control the distal bending mechanism of the surgical instrument. According to an exemplary embodiment, the swash plate is arranged in a steering ring. The first of the two controllable and adjustable motorised drives has a first drive shaft driven by a first motor, which is directly and operatively connected to the steering ring via a first force transmitter, wherein the first force transmitter directly contacts the steering ring at an effective section. For this purpose, the first force transmitter is arranged on the first drive shaft, which defines a first drive axis C. Furthermore, the second of the two controllable and adjustable motorised drives has a second drive shaft driven by a second motor, which is directly and operatively connected to the steering ring via a second force transmitter, wherein the second force transmitter directly contacts the steering ring at the effective section. The second force transmitter is arranged on the second drive shaft, which defines a second drive axis C'.

The steering ring is cardanically suspended on a fastening device which has position sensors on its cardan axes for detecting solid angle values of the steering ring.

"Power transmitter" means any component that directly absorbs the movement initiated by the motor, whether rotary or linear, and can pass it on to the effective section of the steering ring. Frictional solutions are possible, with the rotation of the respective drive shaft being able to be transmitted to the steering ring by means of a friction element, such as a rubber ring. Furthermore, solutions with gear wheels, toothed drive bevel heads, which are in engagement with too things in the active section of the steering ring, are possible. Any kind of direct power transmission is conceivable.

As used herein, "cardan axes" means perpendicular axes defined by the rotational and tilting axes of the cardan suspension of the steering ring, more specifically, the steering ring fastening device. These axes intersect at a point called the "cardan centre" which corresponds to the centre of symmetry of the steering ring. The steering ring is rotated about these axes in its suspension by specific spatial angles of rotation, so that the steering ring tilts in space when rotations are superimposed. The tilting of the steering ring is transferred directly to the steering wires via the swash plate.

"Effective section" is the area of the steering ring that can enter into a force-transmitting operative connection with the force transmitter, i.e., is in direct contact with the force transmitter, e.g., through a frictional operative connection using friction elements, or is in engagement, e.g., through a toothing or other suitable power-transmitting active connections.

The position sensors make it possible to record the spatial rotation angle values, i.e., the angular position of the steering ring in relation to the cardan axes directly on the rotation or tilting axis of the cardan suspension of the steering ring, and thus determine the exact position of the steering ring in space. Possible slippage can also be determined, in particular when a detected tilting of the steering ring deviates from a predetermined tilting. This can be detected using the position sensors.

Advantageously, the steering ring, which includes the swash plate, can be controlled directly by means of the drive motors. This is done via the power transmitters, which are located directly on the drive shafts of the motors. No further deflection mechanisms or gear ratios are necessary, so that the shortest possible transmission chain is possible. Such direct power transmission, which shows linear transmission behaviour, enables simple software control, so that precise control of the component to be controlled is achieved. Using the spatial rotation angle values that can be detected via the position sensors, the control can then be further refined by direct regulation of the drive motors.

A further embodiment of the steering gear according to an exemplary embodiment provides that the fastening device has a housing and a bracket, the bracket being arranged on the side of the bearing ring which is remote from the effective section. The bracket is mounted on the housing at both ends by means of bearing pins and has a receiving opening in the middle, the steering ring being mounted in the receiving opening such that it can rotate about the axis of rotation. The swash plate can be firmly connected to the steering ring, rotatably mounted in the steering ring or also be in one piece with the steering ring, so that a combined component of steering ring and swash plate is created.

Due to the bracket in the bracket, the steering ring can only rotate around its transverse and vertical axis, including overlays. This defines the respective spatial position of the steering ring and prevents rotation about the main axis. The steering ring can be made to be cardan in a structurally simple manner and can be precisely controlled by means of the above-mentioned suspension by means of a bracket. In addition, the steering ring is additionally housed and protected because the bracket spans it.

A further embodiment of the steering gear according to an exemplary embodiment provides that the position sensors are angle sensors or 3D hall sensors. Rotary sensors such as potentiometers or other resistance measuring sensors are suitable as angle sensors. When using two angle sensors, a separate sensor must be installed for each cardan axis, in this case the axis of rotation D of the steering ring and the axis of rotation A of the bracket. In total, these two sensors together can completely record the spatial deflection of the steering ring. It is also possible to arrange additional sensors at other points on the steering gear.

Furthermore, another embodiment of the steering gear according to an exemplary embodiment provides that the housing has a base with passage openings for the drive shafts. The steering gear has a multi-part magnetic sensor, one part of which is arranged between the passage openings in the base of the housing and the second part of which is present in the steering ring in a floating manner above the first part. "Floating" here means that the first part and the second part of the multi-part magnetic sensor are not directly connected to each other, but there is a gap between both parts, i.e., the second part is arranged spaced above the first part. The multi-part magnetic sensor therefore consists of a part that is fixed in the housing and another part that follows the movement of the steering ring. In this case, the first part of the magnetic sensor can detect the change in the second part of the magnetic sensor as a change in position. Various sensors are possible here. In a preferred embodiment of the steering gear, the first part of the multi-part magnetic sensor is a 3D hall sensor and the second part is a bar magnet that is arranged in a recess in the steering ring. With this arrangement, an angular position of the steering ring (and thus its position in space) can be detected by a single position sensor: If the bar magnet moves, a magnetic field change is caused in the hall sensor, which is directly related to the angle of rotation of the bar magnet and thus the angle of rotation of the steering ring. The orientation of the bar magnet can be suitably selected, with the bar magnet preferably being aligned parallel to the main axis B. This orientation is optimal for the angle of deflection of the steering ring to be detected.

Yet another embodiment of the steering gear can provide that the motors each have a motor regulation and control unit, a motor gear, a rotary encoder connected to the respective drive shaft and preferably a slipping coupling. The steering gear can thus be controlled and regulated directly.

According to the first embodiment of a surgical instrument according to an exemplary embodiment, which has a shaft, an actuation unit arranged at the proximal end of the shaft and a tool arranged at the distal end of the shaft with a tool tip that can be bent by means of a distal bending mechanism, which is controlled by means of two controllable and adjustable drives and a spatially adjustable swash plate, the surgical instrument has a steering gear according to an exemplary embodiment for the spatial alignment of the swash plate.

Due to the compact steering gear according to an exemplary embodiment, the surgical instrument can be constructed in a structurally simple and space-saving manner, so that a simple connection to a robot arm can be made possible, in which the movement of the drives can be transmitted directly to the tool tip. The result is that the surgical instrument can be precisely controlled.

According to a further embodiment of the surgical instrument, it is operatively coupled to a regulation and control unit or alternatively to an external data processing unit. The regulation and control unit can be built into the surgical instrument or can be located outside it, for example in a robot arm to which the surgical instrument is to be connected. A controllable use can thus be implemented, depending on the constructive arrangement and structure of the surgical instrument.

A first embodiment of a method according to an exemplary embodiment, for controlling the position of a steering ring of a steering gear according to an exemplary embodiment per se and of the steering gear when it is part of a surgical instrument according to an exemplary embodiment, comprises the steps:

Transmitting predetermined target values of drive angles in relation to an angular position and/or rotation of the drive shafts of the controllable and adjustable motorised drives to the motor regulation and control unit of each motor and bringing the drive shaft into rotation, starting the steering gear and moving the steering ring in the steering gear by rotating the drive shaft, thereby detecting the deflection of the steering gear by detecting the solid angle values of the steering ring using the position sensors and transmitting the detected solid angle values to the motor regulation and control unit, by means of the motor regulation and control unit, converting the detected solid angle values of the steering ring into actual values of the drive angle in relation to an angular position or rotation of the drive shafts, using the motor regulation and control unit, comparing target and actual values of the drive angles in relation to an angular position or rotation of the drive shafts and, if the values differ from one another, depending on the deviation of the target and actual values of the drive angles, correcting the angular position or rotation of the drive shafts.

The method can advantageously detect possible slippage in the power transmission from the drive shafts to the steering ring and thus avoid discrepancies in the control. The control of the steering gear and the surgical instrument is correctable, exact and reproducible, especially when used with direct power transmission, as described by the steering gear according to an exemplary embodiment.

A further embodiment of the method provides for the further step: simultaneously generating a signal in the rotary encoder by rotating the drive shafts, wherein the signal from the rotary encoder is fed back to the motor regulation and control unit. The rotary encoder returns the additional information to the motor control and regulation unit so that it can be checked whether the target values have been correctly adopted and whether the drive shafts specify the correct angle of rotation values. It offers an additional parameter to further improve the control of the steering ring movement.

BRIEF DESCRIPTION OF THE DRAWINGS

Other embodiments of the steering gear, surgical instrument, and method, as well as some of the advantages associated with these and other embodiments, will become apparent and better understood from the following detailed description with reference to the accompanying figures. Items or parts thereof that are substantially the same or similar may be given the same reference numbers. The figures are only a schematic representation of an exemplary embodiment of Showing.

DETAILED DESCRIPTION

Figure 1:
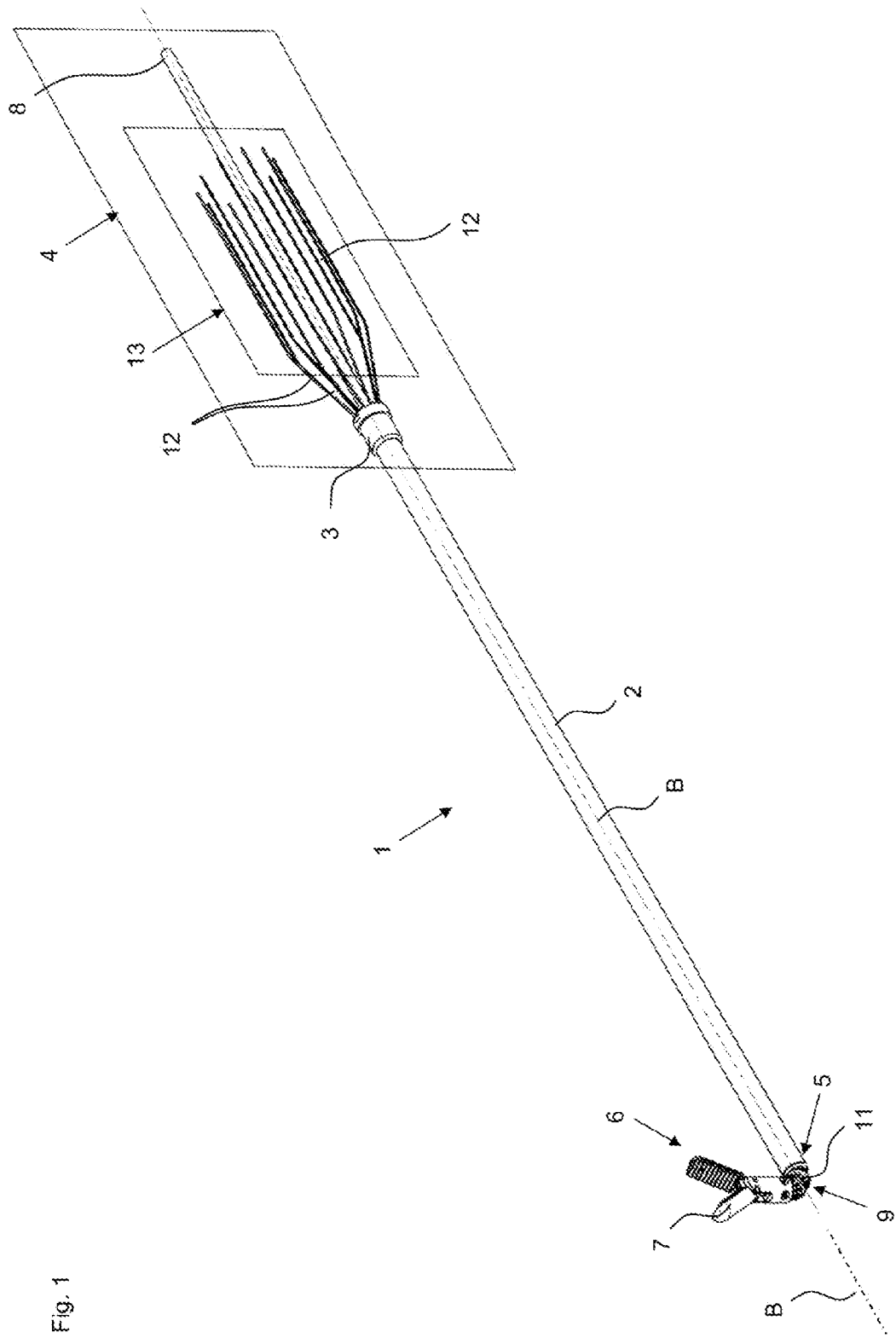
FIG. 1 a perspective view of the surgical instrument with the actuation unit shown schematically, FIG. 2 a detailed view of a first embodiment of the steering gear according to an exemplary embodiment, FIG. 3 a detailed view of the steering gear from FIG. 2 with a housing and bracket in half section, FIG. 4 a detailed view of another embodiment of the steering gear according to an exemplary embodiment with a swash plate and steering ring in half section, and FIG. 5 a flow chart of the method according to an exemplary embodiment for controlling the position of the steering ring.

FIG. 1 schematically shows a surgical instrument 1 with a hollow shaft 2, an actuation unit 4 shown only schematically, arranged at the proximal end 3 of the shaft 2 and a tool tip 6 with a tool 7 arranged at the distal end 5 of the shaft 2. The tool 7 can be actuated via an actuating element 8 which is mounted in an axially displaceable manner in the shaft 2 and which is in operative connection with the actuation unit 4 on the proximal side. The actuation unit 4 can be a manually actuable handle or a structural unit designed for robotic use, i.e., a unit that can also be actuated without manual intervention—which is advantageous for reproducing the actuation. The tool 7 of the tool tip 6 can, for example, be a tool provided with jaw parts, as shown in FIG. 1, or act as an endoscope, an applicator or the like. The instrument tip 6 can be pivoted relative to the longitudinal axis B of the shaft 2 via a joint mechanism 9, wherein the joint mechanism 9 consists of pivoting members 11 arranged at the distal end 5 of the shaft 5, which are connected via guide wires 12 or guide ropes running in the longitudinal direction of the shaft 2 with a drive 13 arranged at the proximal end 3 of the shaft 2, which causes a movement of the drive 13 on the proximal side and corresponding relative movements of the pivoting members 11 on the distal side and thus a pivoting of the instrument tip 6. Even if only the term steering wires 12 is used above and below, steering cables can also be used functionally, which is why the term steering wires 12 used should also be read and understood synonymously as a steering cable.

The actuating element 8, which is mounted so that it can be displaced axially in the shaft 2 for actuating the tool 7, which consists of two jaw parts for example, is designed as a push/pull rod in the illustrated embodiment.

The drive 13 for the steering wires 12 can be designed as a motorised drive 13 in the surgical instrument 1 according to an exemplary embodiment, which has a spatially adjustable swash plate 14 (dashed in FIG. 1), which is cardanically mounted via components such as brackets or steering rings in order to three-dimensionally displace the swash plate 14 relative to the longitudinal axis B of the shaft 2. The steering wires 12 are mounted or attached to the swash plate 14 in such a way that a displacement of the swash plate 14 caused by the motorised drive 13 causes the tool tip 6 to pivot via the steering wires 12. The number of steering wires 12 to be used for a motorised drive 13 can be freely selected. The steering wires 12 of the swash plate 14 running parallel to the longitudinal axis B of the shaft 2 can be guided into the shaft 2 via serrated lock washers (not illustrated) or a guide element (not illustrated) that widens the steering wires 12.

Figure 2:
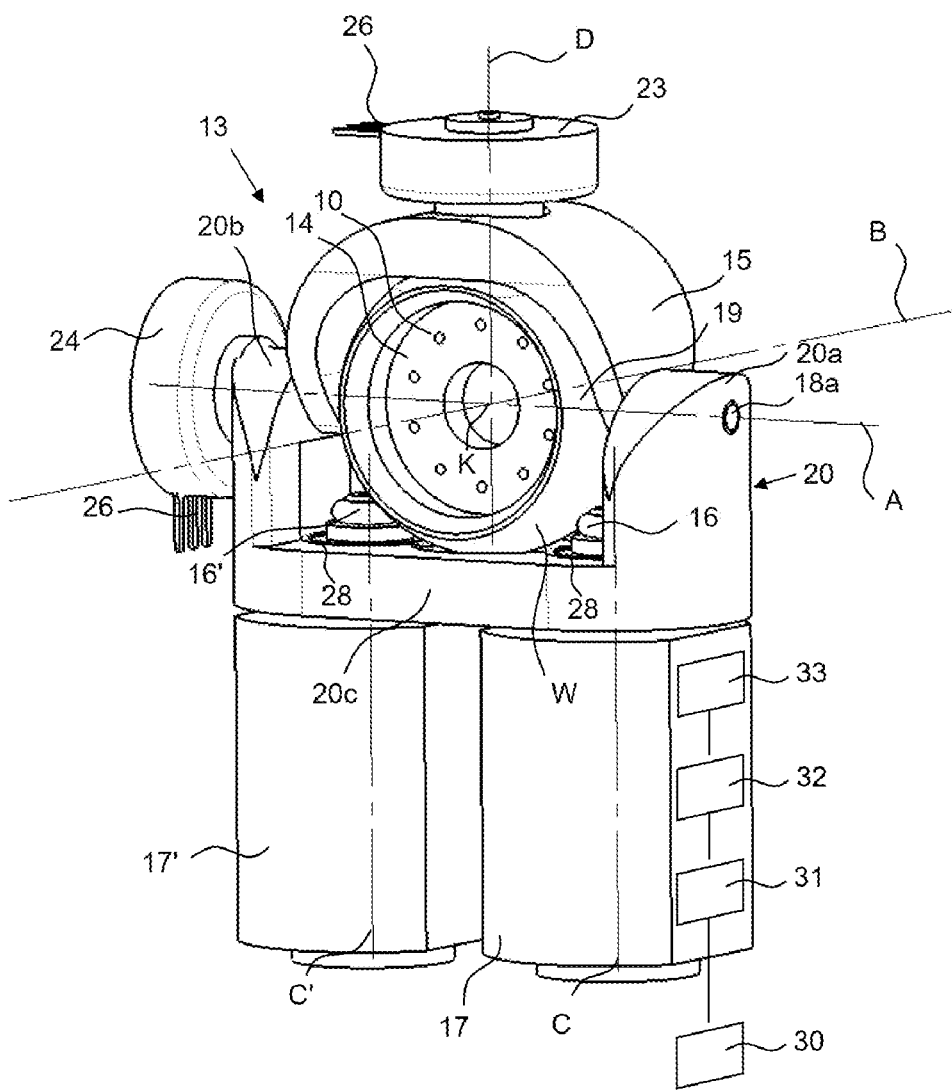
Figure 3:
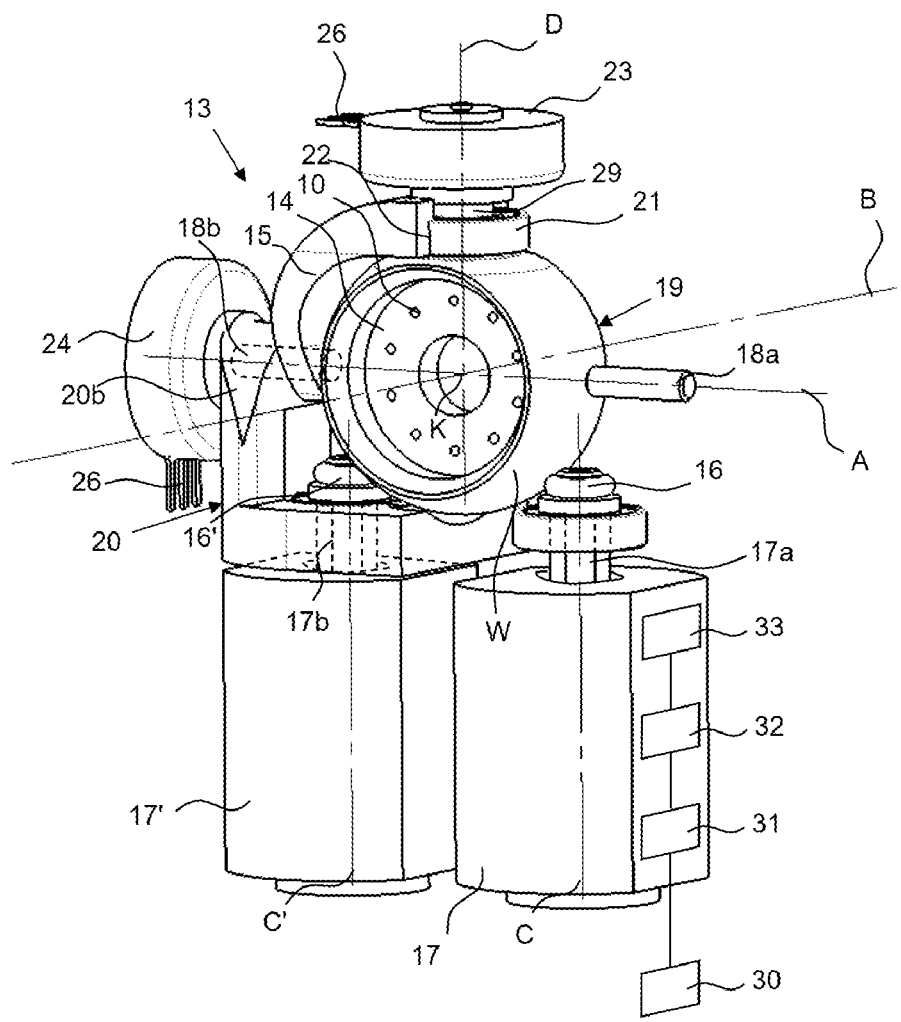
Figure 4:
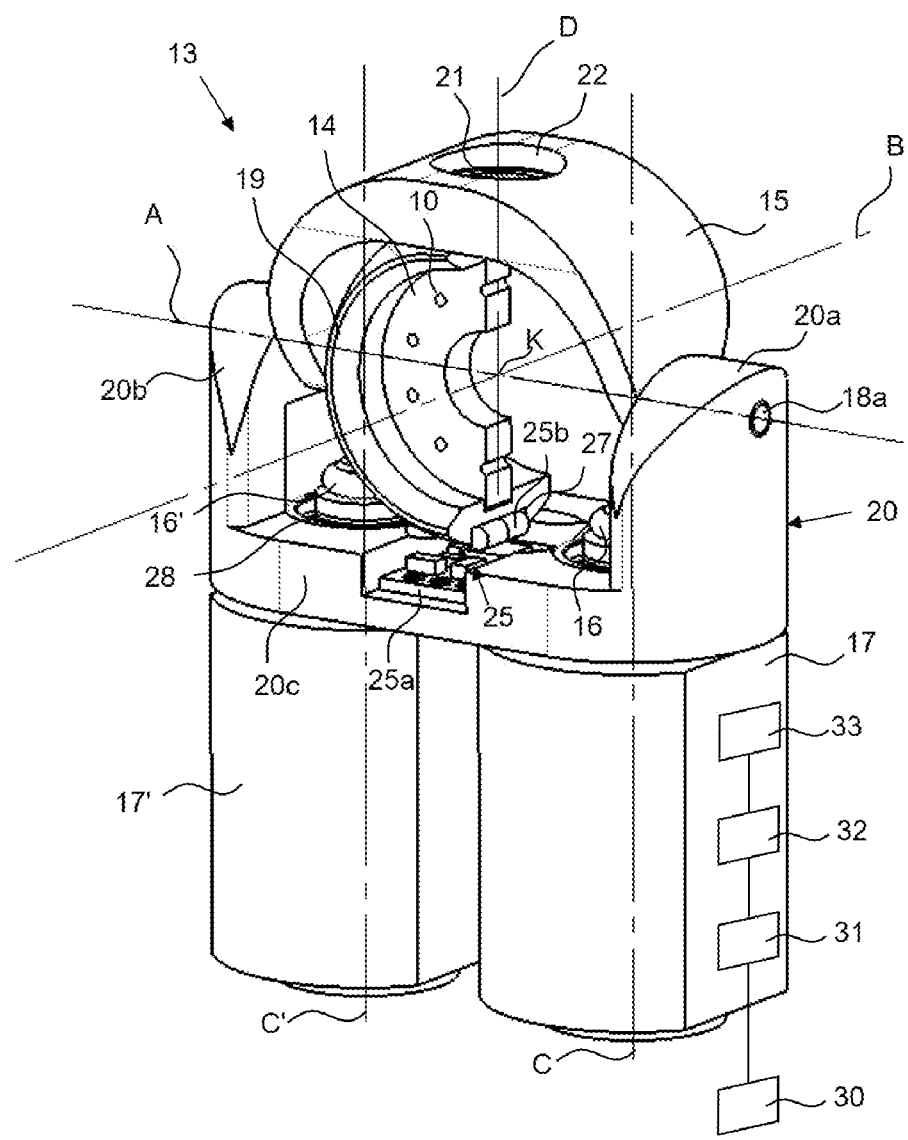

The surgical instrument 1 or essential moving parts thereof are electronically connected to a control and regulation unit 34 (shown in FIG. 1 with the dashed square). This can be arranged in a housing of the surgical instrument 1 or in a robot arm to be connected to the surgical instrument 1.

in FIGS. 2, 3 and 4, the steering gear 13 according to an exemplary embodiment shown has a housing 20 which is essentially formed from two opposite lateral housing parts 20*a*, 20*b* and a housing base 20*c*. The lateral housing parts 20*a*, 20*b* form a bearing for a bracket 15 which is rotatably mounted via bearing pins 18*a*, 18*b* in corresponding bores in the lateral housing parts 20*a*, 20*b*, here through bores. The swash plate 14, which is surrounded by a steering ring 19 along its circumference, is arranged between the lateral housing parts 20*a*, 20*b*.

The steering ring 19 is spanned by the bracket 15 and is rotatably held about an axis of rotation D in a passage opening 22 in the bracket 15 by means of a bearing ring 21. For this purpose, the steering ring 19 has a holding piece 29 which is held in the bearing ring 21.

Below the housing base 20*c* of the housing 20, two motors 17, 17' are arranged, the drive axes C, C' of which are parallel to one another and, in the illustrated neutral position of the steering ring 19, parallel to the axis of rotation D of the steering ring 19. The motors 17, 17' have drive shafts 17*a*, 17*b* extending through passage openings 28 in the housing base 20*c*.

FIGS. 2, 3 and 4 show that force transmitters 16, 16' are arranged on the drive shafts 17*a*, 17*b*, which transfer the rotational movement of the drive shafts 17*a*, 17*b* into a rotating/tilting movement on the steering ring 19. Each force transmitter 16, 16' is coupled to the steering ring 19, preferably in a lower region of the steering ring 19 shown in the figures, which forms an effective section W there. In the effective section W, the direct transmission of force between the force transmitter 16, 16' and the steering ring 19 takes place. The steering ring 19 is a part-spherical shell and thus has a part-spherical shape, particularly in the effective section W, in order to coordinate its movements. The movements are initiated by the force transmitters 16, 16', which are arranged parallel to the axis of rotation D of the steering ring 19. The axis of rotation D and the axis of rotation A of the bracket 15 cross each other at a crossing point K, which forms the cardan centre of the cardan suspension.

In FIGS. 2 and 3, the steering gear 13 shown has position sensors 23, 24 on each of its cardan axes A, D. The position sensor 23, which is connected to the holding piece 29 of the steering ring 19, measures the angular position of the steering ring 19 in the bracket 15 about the axis D. The position sensor 24, which engages with the bearing pin 18*b* on the axis of rotation A, detects the angular position of the bracket 15 about the axis A. Angle sensors, for example potentiometers, are particularly suitable for this purpose. If both detected angular positions are taken together, the position of the steering ring 19 in space is obtained.

By means of electrical connectors 26, such as plugs or soldering lugs, the position sensors 23, 24 with the control and regulation unit 34 of the surgical instrument 1 (FIG. 1).

In FIG. 4 the steering gear 13 is equipped with a multi-part magnetic sensor 25. The multi-part magnetic sensor 25 has a first part 25*a* which is arranged between the passage openings 28 in the base 20*c*. A second part 25*b* of the multi-part magnetic sensor 25 is inserted above the first part 25*a* in a recess 27 in the casing part of the steering ring 19. The first part 25*a* consists of electronics with a circuit board that forms the base part of a 3D hall sensor. The second part 25*b* is a bar magnet which is completely received in the recess 27 of the steering ring 19. The two parts 25*a*, 25*b* are not connected, but spaced apart from each other, so that the second part 25*b* hovers over the first part 25*a*. If the bar magnet 25*b* moves, a magnetic field change is caused in the hall sensor 25*a*, which is directly related to the angle of rotation of the bar magnet 25*b* and thus the angle of rotation of the steering ring 19. The orientation of the bar magnet 25*b* is aligned parallel to the main axis B in FIG. 4.

Furthermore, each of the motors 17, 17' has a motor regulation and control unit 30, a motor gear 31, a rotary encoder 32 connected to each drive shaft 17*a*, 17*b*, and a slipping coupling 33.

Figure 5:
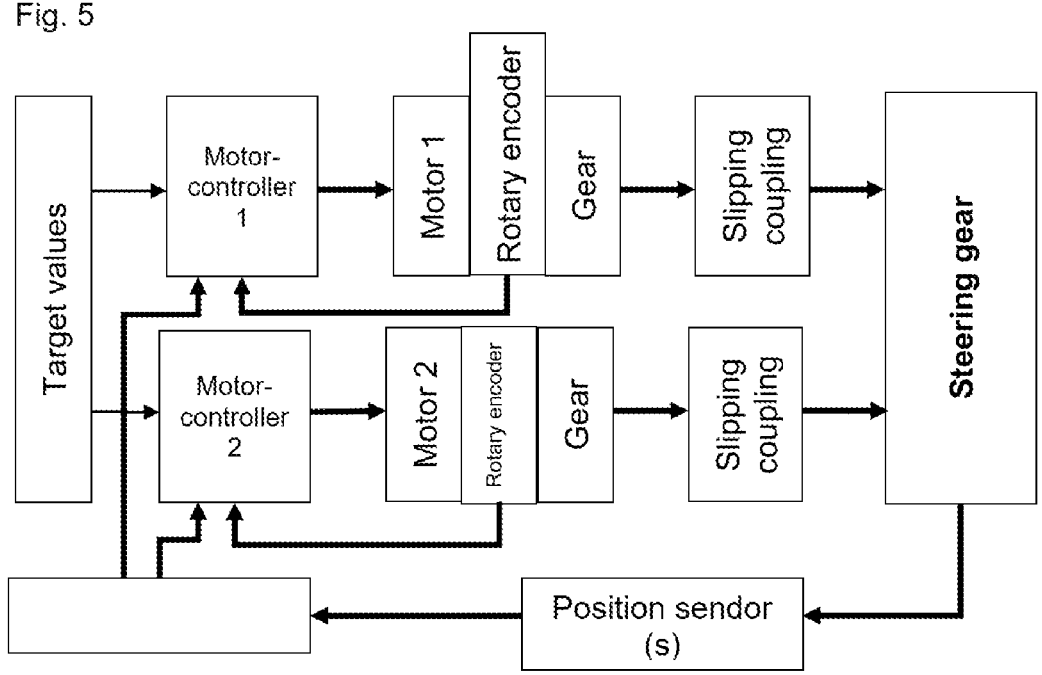

In FIG. 5 a sequence of the method according to an exemplary embodiment for controlling a position of the steering ring is shown schematically. For the sake of a better overview, only the part that is essential for the method is explained; a complete description of a conventional motor control circuit has been omitted, the control circuit is known to the person skilled in the art. In a first step, predetermined target values of drive angles in relation to an angular position of the drive shafts 17*a*, 17*b* of the motors 17, 17' are transmitted to the motor control unit 30 of each motor 17, 17' and one or both of the drive shafts 17*a*, 17*b* is/are set in rotation.

At the same time, the rotation of the drive shaft 17*a*, 17*b* by the motor gear 31 generates a signal in the rotary encoder 32 which is fed back to the motor regulation and control unit 30.

By turning the drive shaft 17*a*, 17*b*, the steering gear 19 is set in motion and the steering ring 19 is moved in the steering gear 13.

The rotation of the steering ring 19 or its angle of rotation or solid angle values is detected by the position sensors 23, 24, 25 and thus the deflection of the steering gear 13. These recorded solid angle values are transmitted to the motor regulation and control unit 30.

In the motor regulation and control unit 30, the detected solid angle values of the steering ring 19 are recalculated into actual values of the drive angles of the drive shafts 17*a*, 17*b* by means of a mathematical construct, in the inverse kinematic problem.

In the motor regulation and control unit 30, the setpoint and actual values of the drive angles are then compared and if the values differ from one another, the angular position of the drive shafts 17*a*, 17*b* is corrected depending on the deviation of the setpoint and actual values of the drive angles of the drive shafts 17*a*, 17*b*.

The corrected angular position acts on the steering ring 19 and is thus transmitted to the steering gear 13 so that, for example, slippage between the force transmitters 16, 16' and the steering ring 19 can be detected and prevented.

LIST OF REFERENCE NUMBERS

1 Surgical instrument
2 Shaft
3 Proximal end of the shaft
4 Actuation unit
5 Distal end of the shaft
6 Tool tip
7 Tool
8 Actuator
9 Joint mechanism
10 Housing
11 Pivoting member
12 Steering wires 13 Steering gear
14 Swash plate
15 Bracket
16, 16' Power transmitter
17, 17' Motor
17a, 17b Drive Shaft motors
18a, 18b Bearing pins bracket
19 Steering ring
20 Housing
20a, 20b Lateral housing parts
20c Case base
21 Bearing ring
22 Opening
23 Position sensor
24 Position sensor
25 Position sensor/multi-part magnetic sensor
25a First part of the multi-part magnetic sensor
25b Second part of multi-part magnetic sensor
26 Electrical connector
27 Recess
28 Passage opening
29 Holding piece
30 Motor regulation and control unit
31 Motor gear
32 Rotary encoder
33 Slipping coupling
34 Control and regulation unit of the surgical instrument
A Axis of rotation bracket
B Main axis instrument
C, C' Drive axes
D Axis of rotation steering ring
W Effective section

The invention claimed is:

1. A steering gear for a surgical instrument, which can be arranged at the proximal end of a shaft that defines a longitudinal axis and has a bending mechanism at the distal end,
wherein the steering gear has two controllable and adjustable motorised drives and is designed to transfer the adjustment angles of the two controllable and adjustable motorised drives to a spatial alignment of a swash plate which is designed to control the distal bending mechanism of the surgical instrument, wherein
the swash plate is arranged in a steering ring, wherein
the first of the two controllable and adjustable motorised drives has a first drive shaft driven by a first motor, which is directly and operatively connected to the steering ring via a first force transmitter, wherein the first force transmitter directly contacts the steering ring at an effective section, wherein the first power transmitter is disposed on the first drive shaft defining a first drive axis, and
the second of the two controllable and adjustable motorised drives has a second drive shaft driven by a second motor, which is directly and operatively connected to the steering ring via a second force transmitter, wherein the second force transmitter directly contacts the steering ring at the effective section, wherein the second force transmitter is disposed on the second drive shaft defining a second drive axis, wherein
the steering ring is cardanically suspended on a fastening device, and wherein the fastening device has position sensors on its cardan axes.

2. The steering gear according to claim 1, wherein
the fastening device has a housing and a bracket, the bracket being arranged on the side of the steering which faces away from the effective section and is mounted on both ends on the housing by means of bearing pins and has a receiving opening in the middle,
wherein the steering ring is rotatably mounted in the receiving opening about the axis of rotation.

3. The steering gear according to claim 1, wherein
the position sensors are angle sensors or 3D hall sensors.

4. The steering gear according to claim 2, wherein
the housing has a base with passage openings for the drive axes, and wherein
the steering gear has a multi-part magnetic sensor, one part of which is arranged between the passage openings in the base and the second part of which is suspended above the first part in the steering ring.

5. The steering gear according to claim 4, wherein
the first part of the multi-part magnetic sensor is a 3D hall sensor, and the second part is a bar magnet which is arranged in a recess of the steering ring.

6. The steering gear according to claim 1, wherein
the motors each have a motor regulation and control unit, a motor gear, a rotary encoder connected to each drive shaft and preferably a slipping coupling.

7. A surgical instrument having a shaft, an actuation unit arranged at the proximal end of the shaft and a tool arranged at the distal end of the shaft with a has a tool tip that can be bent by means of a distal bending mechanism and can be controlled by a swash plate that can be spatially aligned by means of two controllable and adjustable drives, wherein
the surgical instrument has a steering gear according to claim 1 for the spatial alignment of the swash plate.

8. The surgical instrument according to claim 7, wherein
the surgical instrument is operatively coupled to a regulation and control unit.

9. A method for controlling the position of a steering ring of a steering gear according to claim 1 and in a surgical instrument, wherein
transmitting predetermined target values of drive angles in relation to an angular position and/or rotation of the drive shafts of the controllable and adjustable motorised drives to the motor regulation and control unit of each motor and bringing the drive shaft into rotation,
simultaneously generating a signal in the rotary encoder by rotating the drive shafts, wherein the signal from the rotary encoder is fed back to the motor regulation and control unit,
starting the steering gear and moving the steering ring in the steering gear by rotating the drive shaft,
thereby detecting the deflection of the steering gear by detecting the solid angle values of the steering ring using the position sensors and transmitting the detected solid angle values to the motor regulation and control unit,
by means of the motor regulation and control unit converting the detected solid angle values of the steering ring into actual values of the drive angle,
by means of the motor regulation and control unit comparing target and actual values of the drive angles and, if the values differ from one another, depending on the deviation of the target and actual values of the drive angles, correcting the angular position and/or rotation of the drive shafts.

* * * * *